United States Patent [19]

Pifferi

[11] 3,976,673

[45] Aug. 24, 1976

[54] 4-CYCLOPROPYLMETHYLENEOXY-3-CHLOROPHENYLACETIC ACID AND SALTS THEREOF

[75] Inventor: Giorgio Pifferi, Milan, Italy

[73] Assignee: ISF SpA, Milan, Italy

[22] Filed: Jan. 9, 1975

[21] Appl. No.: 539,912

[30] Foreign Application Priority Data

Jan. 14, 1974 Italy .................... 19366/74

[52] U.S. Cl. .................. 260/438.1; 260/501.1; 260/501.14; 260/501.15; 260/501.2; 260/520 R; 260/999; 424/294; 424/316; 424/317

[51] Int. Cl.$^2$ .................. C07C 63/52; C07C 87/14; C07F 1/08

[58] Field of Search ........ 260/520 R, 501.1, 501.11, 260/501.12, 438.1, 473 R, 501.14, 501.15, 501.2; 424/294, 316, 317

[56] References Cited

UNITED STATES PATENTS

| | | | |
|---|---|---|---|
| 3,553,226 | 1/1971 | Kaiser et al. | 260/520 R |
| 3,766,263 | 10/1973 | Godfrey | 260/520 R |
| 3,786,085 | 1/1974 | Dickel et al. | 260/520 R |

FOREIGN PATENTS OR APPLICATIONS

1,174,535   12/1969   United Kingdom ............ 260/520 R

*Primary Examiner*—Norman Morgenstern
*Attorney, Agent, or Firm*—Stevens, Davis, Miller & Mosher

[57] ABSTRACT

The compound 4-cyclopropylmethyleneoxy-3-chlorophenylacetic acid and its non-toxic pharmaceutically acceptable salts have activity as anti-inflammatory, antipiretic and analgesic agents. It is prepared by reacting a lower alkyl ester of 3-chloro-4-hydroxyphenyl acetic acid with a cyclopropylmethylene halide and subsequently saponifying the ester obtained. The acid obtained is optionally salified to give corresponding non-toxic, inorganic or organic pharmaceutically acceptable salts.

4 Claims, No Drawings

4-CYCLOPROPYLMETHYLENEOXY-3-CHLOROPHENYLACETIC ACID AND SALTS THEREOF

The present invention relates to a biologically active derivative of phenylacetic acid, as well as its salts and the process for the preparation thereof.

The present invention further relates to pharmaceutical compositions containing said derivative of phenylacetic acid, as such or in the form of a salt, in mixture with suitable excipients. More particularly, the invention relates to 4-cyclopropylmethyleneoxy-3-chlorophenyl-acetic acid and to its non-toxic pharmaceutically acceptable salts with alkali and alkaline earth metals 1 copper suitable organic bases: this compound and its salts have activity as anti-inflammatory, antipiretic and analgesic agents.

Some derivatives of phenylacetic acid have been described in the literature, which possess a biological pattern qualitatively similar to that of 4-cyclopropylmethyleneoxy-3-chlorophenylacetic acid of the present invention. Compared to them, the latter shows besides noticeable stability of its chemical structure, remarkable enhancement of the biological activity and a constantly higher therapeutical index.

The process for the preparation of 4-cyclopropylmethyleneoxy-3-chlorophenylacetic acid of the present invention comprises reacting at elevated temperatures under anhydrous conditions a lower alkyl ester of 3-chloro-4-hydroxyphenylacetic acid with a cyclopropylmethylene halide and subsequently saponifying the ester obtained. The process produces high yields, and the 4-cyclopropylmethyleneoxy-3-chlorophenylacetic acid obtained has the appearance of a chemically stable crystalline solid.

Suitable non-toxic pharmaceutically acceptable salts of the acid are those of alkali and alkaline earth metals such as sodium, potassium, calcuim and magnesium, ammonium or copper salt, and with organic bases, particularly with basic amino-acids, such as ornithine, lysine, arginine and histidine. These salts may be prepared in known manner by reacting the acid with a suitable base or by double exchange from a suitable salt.

By the term "lower alkyl" there is meant a linear alkyl radical containing from 1 to 3 carbon atoms. The compound and its non-toxic pharmaceutically acceptable salts can be administered internally, for example, parenterally or enterally in conventional pharmaceutical dosage forms. For example, they can be incorporated in conventional liquid or solid vehicles such as water, gelatin, starch, magnesium stearate, talc, vegetable oils and the like to provide tablets, elixirs, capsules, solutions, and emulsions, according to acceptable pharmaceutical practice.

The following example which is in no way limitative, serves to illustrate the invention.

EXAMPLE 4-cyclopropylmethyleneoxy-3-chlorophenylacetic acid

A mixture of 10.6 g methyl 3-chloro-4-hydroxyphenylacetate, 13.5 g cyclopropylmethylene bromide and 13.8 g anhydrous potassium carbonate in 200 ml acetone is refluxed under stirring for 20 hours. The solvent is removed by distillation in vacuo on a water-bath, and the residue taken up with 60 ml distilled water and extracted twice with ethyl ether. The ethereal extracts are collected, washed with cold dilute sodium hydrate, then with water and made anhydrous on magnesium sulphate.

After evaporation of the solvent, 12.7 g ethyl-4-cyclopropylmethyleneoxy-3-chlorophenylacetate are obtained in the form of strawcoloured oil. The compound so obtained is added to a solution of 27.5 ml ethanol and 27.5 ml 2N sodium hydrate and heated to ebullition for 2 hours. The mixture is concentrated in vacuo until dry and the residue dissolved in water, cooled and acidified with 50% sulphuric acid to Congo red.

The white precipitate so obtained is extraced twice with ether and the ethereal extracts collected together, washed with water and made anhydrous on magnesium sulphate. The resulting solution is filtered, the solvent evaporated and the residue crystallized from cyclohexane obtaining 11.4 g of 4-cyclopropylmethyleneoxy-3-chlorophenylacetic acid in the form of a crystalline white solid melting at 105°–106°C.

Copper salt. - Grams 7.2 4-cyclopropylmethyleneoxy-3-chlorophenylacetic acid are dissolved in 30 ml of a sodium bicarbonate solution. To said solution is added dropwise and with stirring a solution of copper acetate. The mixture is left under stirring for half an hour, the solid collected by filtration, washed with warm water until neutral reaction, and dried on a waterbath until constant weight. Grams 4.5 copper 4-cyclopropylmethyleneoxy-3-chlorophenylacetate melting at 198°–200°C are obtained.

DL-lysine salt - Grams 2.4 4-cyclopropylmethyleneoxy-3-chlorophenylacetic acid are dissolved in 20 ml absolute alcohol. To said solution are added 3 g of a 50% DL-lysine aqueous solution. The mixture is left to stand for half an hour, after which the gelatinous white precipitate obtained is filtered and dried in vacuo. Grams 3.80 DL-lysine 4-cyclopropylmethyleneoxy-3-chlorophenylacetate are obtained which, recrystallized from 95% ethyl alcohol, melts at 175°–6°C.

4-Cyclopropylmethyleneoxy-3-chlorophenylacetic acid and its salts, according to the present invention, possess anti-inflammatory, antipiretic and analgesic activity, as well as low toxicity. These activities have been evaluated by a comparative study carried out with the product of this invention and its copper and lysine salts at a dosage expressed as acid and phenylbutazone or 4-butyl-1,2-diphenyl-3,5-dioxopyrazoline, known throughout the world as an anti-inflammatory, antipiretic and analgesic agent and 4-allyloxy-3-chlorophenylacetic acid which is structurally the most similar known compound in the art to the compound of this invention.

Analgesic activity

It was evaluated according to the following methods:
a. Randall and Selitto

The pressure to be exerted on a rat's paw previously made edematous by injecting into the plantar zone 0.1 ml of 20% suspension of yeast until appearance of painful reaction was measured in mmHg. The pain threshold was determined 30 minutes before and 30, 60, 90 and 120 minutes after the administration of the substances under test. 10 Male Wistar rats weighing 170–190 g were used for each dosage level and the corresponding average values considered for each dose. The percentage increase of the pain threshold compared to the basal values is taken as the index of the analgesic activity. The results obtained are reported in Table I.

10 Animals were used for each dosage level. The increase difference in the volume of the paw of animals

TABLE I

| Dose mg/kg | Route | 4-allyloxy-3-chloro-phenylacetic acid | % Increase of pain threshold 4-cyclopropyl-Methylencoxy-3-chlorophenyl-acetic acid | Copper 4-cyclo-propylmethylene-oxy-3-chloro-phenylacetate | DL-lysine 4-cyclopropyl-methyleneoxy-3-chloro-phenylacetate | phenyl-butazone |
|---|---|---|---|---|---|---|
| 25 | i.p. | 7 | 27 | 67 | 83 | 3 |
| 50 | i.p. | 30 | 105 | 121 | 103 | 42 |
| 100 | i.p. | 93 | 176 | | | 105 |
| 25 | os | 15 | 44 | 62 | 30 | 33 |
| 50 | os | 57 | 120 | 116 | 104 | 94 |
| 100 | os | 92 | 180 | | | 111 | b. Siegmund

The antagonism towards the abdominal stretching induced by phenylbenzoquinone was evaluated. Swiss male mice weighing 19–21 g were treated orally with the compounds under examination 30 minutes before the endoperitoneal administration of 0.25 ml of a 1.02% aqueous phenylbenzoquinone solution. The animals were kept under observation for 30 minutes after treatment with phenylbenzoquinone and the abdominal stretchings for each animal were counted. 10 Mice for each dosage level were used and the corresponding average values considered. The percentage decrease of the number of abdominal stretchings in the animals treated with the substances under test compared with the controls treated with water was taken as the index of the analgesic activity.

The results obtained are reported in Table 2.

treated compared with the controls represents the index of the anti-inflammatory activity. The results obtained, expressed as percentage inhibition of the volume of the edema compared to the controls and evaluated as average value for each dose are listed in Table 3.

TABLE 3

| Dose mg/kg | Route | 4-allyloxy-3-chloro-phenylacetic acid | % Inhibition of oedema 4-cyclopropyl-methyleneoxy-3-chlorophenyl-acetic acid | copper 4-cyclo-propylmethylene-oxy-3-chloro-phenylacetate | DL-lysine 4-cyclopropyl-methyleneoxy-3-chloro-phenylacetate | phenyl-butazone |
|---|---|---|---|---|---|---|
| 2.5 | i.p. | 0 | 15 | | | 0 |
| 5 | i.p. | 10 | 37 | 32 | 38 | 3 |
| 25 | i.p. | 25 | 55 | 51 | 64 | 22 |
| 50 | i.p. | 57 | 61 | 61 | | 55 |
| 10 | os | 18 | 31 | 38 | 41 | 0 |
| 50 | os | 34 | 65 | 71 | 81 | 28 |

TABLE 2

| Dose mg/kg | Route | 4-allyloxy-3-chloro-phenylacetic acid | % Decrease in number of stretchings 4-cyclopropyl-methyleneoxy-3-chlorophenyl-acetic acid | Copper 4-cyclopropyl-methyleneoxy-3-chlorophen-ylacetate | DL-lysine 4-cyclopropyl-methyleneoxy-3-chloro-phenylacetate | phenyl-butazone |
|---|---|---|---|---|---|---|
| 25 | os | 27 | 51 | 50 | 60 | 3 |
| 50 | os | 58 | 77 | 81 | 90 | 65 |
| 100 | os | 96 | 98 | 99 | 100 | 98 |

Anti-inflammatory activity

This was determined according to Winter's method which evaluates the inhibiting effect on the edema induced by carrageenin.

Male rats weighing 170–190 g were treated with the compounds under test and after 60 minutes 0.005 ml of a 1% aqueous solution of carrageenin were injected into the plantar zone of a hind paw of each animal. The volume of the treated paw was determined immediately after the injection and 3 hours later.

Anti-piretic activity

This was evaluated considering 2 kinds of hyperpyressia. Hyperpyressia induced by:

a. bactopeptone

1 Milliliter of 5% aqueous solution of bactopeptone preincubated for 18 hours at 37°C were injected subcutaneously in Wistar male rats weighing 170–190 g. 4 Hours after treatment with the pyrogen, the animals were divided into groups of ten animals each and treated orally with the substances under examination. The rectal temperature was taken at the beginning of the test, 4 hours after the injection of the pyrogen agent and subsequently 1, 2 and 3 hours after the administration of the substances under test. The difference between the temperature taken in the treated animals and in controls is an index of the anti-pyretic activity.

b. yeast

To albino rabbits, 1 ml/kg of a 0.2% aqueous suspension of yeast were injected intravenously. The rectal temperature was teken at the beginning of the experiment and 60 minutes after the treatment with the pyrogen agent. Immediately after taking the temperature the compounds under test were administered orally to the animals and the rectal temperatures thereof were subsequently measured after 30, 60, 120 and 180 minutes. 10 Animals were treated for each dose level. The difference between the temperatures taken in the animals treated and in the controls is and index of the antipyretic activity. The results obtained by performing the two methods cited above for the determination of the antipyretic activity are listed in Tables 4 and 5 respectively and evaluated as average value for each dose.

for obvious modifications will be apparent to those skilled in the art.

What is claimed is:

1. 4-Cyclopropylmethyleneoxy-3-chlorophenylacetic acid and its non-toxic pharmaceutically acceptable salts of alkali and alkaline earth metals, copper and organic bases.

2. Copper 4-cyclopropylmethyleneoxy-3-chlorophenylacetate.

3. DL-lysine 4-cyclopropylmethyleneoxy-3-chlorophenylacetate.

TABLE 4

| basal temperature | temperature 4 hours after administration of pyrogen | test compound os | dose mg/kg | Rectal temperature in °C | | |
|---|---|---|---|---|---|---|
| | | | | 1 hour after treatment | 2 hours after treatment | 3 hours after treatment |
| 36.7 | 38.6 | controls | | 38.9 | 39.2 | 38.9 |
| 36.5 | 38.7 | 4-allyloxy-3-chloro- | 15 | 38.2 | 38.7 | 38.4 |
| 36.6 | 38.4 | phenylacetic acid | 25 | 37.6 | 38.4 | 38.5 |
| 37.4 | 39.0 | | 50 | 37.7 | 37.5 | 37.7 |
| 36.2 | 38.7 | 4-cyclopropylmethylene- | 6 | 38.7 | 39.3 | 39.1 |
| 36.4 | 38.4 | oxy-3-chlorophenylacetic | 15 | 37.7 | 38.0 | 37.6 |
| 36.5 | 38.3 | acid | 25 | 37.3 | 37.3 | 37.1 |
| 36.3 | 38.9 | copper 4-cyclopropyl- | 15 | 38.1 | 37.7 | 36.7 |
| 36.3 | 38.8 | methyleneoxy-3-chloro-phenylacetate | 25 | 37.8 | 37.2 | 36.6 |
| 36.4 | 38.8 | DL-lysine-4-cyclopropyl- | 15 | 37.6 | 38.0 | 37.8 |
| 35.9 | 38.8 | methyleneoxy-3-chloro-phenylacetate | 25 | 37.4 | 37.0 | 36.7 |
| 37.1 | 38.6 | phenylbutazone | 15 | 38.3 | 38.8 | 38.6 |
| 36.8 | 38.7 | | 25 | 38.1 | 38.9 | 38.3 |
| 37.1 | 39.2 | | 100 | 38.1 | 37.6 | 37.4 |

TABLE 5

| basal temperature | temperature 60 mins. after administration of pyrogen | test compound per os | dose mg/kg | Rectal temperature in °C | | | |
|---|---|---|---|---|---|---|---|
| | | | | 30 mins. after treatment | 60 mins. after treatment | 120 mins. after treatment | 180 mins. after treatment |
| 39.33 | 39.97 | controls | | 40.61 | 40.53 | 40.33 | 40.15 |
| 39.20 | 40.16 | 4-allyloxy-3-chloro- | 10 | 40.30 | 40.13 | 40.06 | 40.03 |
| 39.65 | 40.00 | phenylacetic acid | 25 | 40.35 | 39.85 | 39.30 | 39.25 |
| 38.81 | 39.45 | 4-cyclopropylmethylene- | 5 | 40.17 | 40.15 | 40.55 | 40.02 |
| 39.17 | 39.68 | oxy-3-chlorophenylacetic | 10 | 40.05 | 39.90 | 39.48 | 39.32 |
| 39.55 | 40.10 | acid | 25 | 40.65 | 39.95 | 39.20 | 39.05 |

The foregoing detailed description has been given for clarity of understanding only and no unnecessary limitations are to be understood therefrom. The invention is not limited to the exact details shown and described 4. A composition comprising an excipient plus an analgesically, antipuretically or antiinflammatorily effective amount of the compound as defined in claim 1.

* * * * *

UNITED STATES PATENT AND TRADEMARK OFFICE
CERTIFICATE OF CORRECTION

PATENT NO. : 3,976,673
DATED : August 24, 1976
INVENTOR(S) : Giorgio PIFFERI

It is certified that error appears in the above-identified patent and that said Letters Patent are hereby corrected as shown below:

IN THE ABSTRACT:

line 4, correct the spelling of "antipyretic".

IN THE SPECIFICATION:

Column 1, line 15, change "metals 1 copper suitable" to --metals, copper or suitable--;

Column 1, line 16, change "antipi-" to -- antipy- --;

Column 1, line 38, correct the spelling of "calcium".

Column 2, line 13, correct the spelling of "extracted";

Column 2, line 48, change "dioxopyrazoline" to --dioxopyrazolidine--;

Column 2, line 49, change "antipi-" to -- antipy- --.

Column 3, line 35, change "1.02%" to --0.02%--;

Column 3, line 64, change "0.005 ml" to --0.05 ml--.

Column 4, line 36, change "Anti-piretic activity" to --Anti-pyretic activity--;

Column 4, line 66, correct the spelling of "taken".

Column 5, line 6, change "and" in the second occurrence to --an--.

UNITED STATES PATENT AND TRADEMARK OFFICE
CERTIFICATE OF CORRECTION

PATENT NO. : 3,976,673

DATED : August 24, 1976

INVENTOR(S) : Giorgio PIFFERI

It is certified that error appears in the above-identified patent and that said Letters Patent are hereby corrected as shown below:

Column 6, line 45, (line 2 of claim 4), change "antipuretically" to --antipyretically--.

Signed and Sealed this

Nineteenth Day of April 1977

[SEAL]

Attest:

RUTH C. MASON
*Attesting Officer*

C. MARSHALL DANN
*Commissioner of Patents and Trademarks*